United States Patent [19]

Treuner

[11] Patent Number: 4,551,277
[45] Date of Patent: Nov. 5, 1985

[54] 4-(3-ACYLAMINO-2-OXO-1-AZETIDINYL)-4-OXO-2-BUTENOIC ACID

[75] Inventor: Uwe D. Treuner, Regensburg, Fed. Rep. of Germany

[73] Assignee: E. R. Squibb & Sons, Inc., Princeton, N.J.

[21] Appl. No.: 550,288

[22] Filed: Nov. 9, 1983

[51] Int. Cl.$^4$ ............... C07D 205/08; A61K 31/395; C07D 403/12; C07D 401/12
[52] U.S. Cl. .................... 260/239 A; 260/239.3 R; 260/245.4; 260/330.3; 260/330.9; 544/182; 544/215; 544/279; 544/335; 544/336; 544/359; 544/327; 546/187; 546/208; 546/256; 546/275; 514/210
[58] Field of Search ............ 260/239 A, 245.4, 330.3, 260/330.9, 239.3 R; 544/182, 215, 279, 327, 335, 336, 359; 546/187, 208, 256, 275

[56] References Cited

FOREIGN PATENT DOCUMENTS 2071650 9/1981 United Kingdom ........... 260/239 A

Primary Examiner—Mark L. Berch
Attorney, Agent, or Firm—Lawrence S. Levinson; Donald J. Barrack

[57] ABSTRACT

Antibacterial activity is exhibited by (3-acylamino)-2-azetidinones having in the 1-position a group of the formula

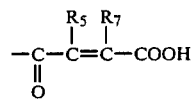

or a salt or ester thereof wherein $R_5$ and $R_6$ are the same or different and each is hydrogen or alkyl.

8 Claims, No Drawings

4-(3-ACYLAMINO-2-OXO-1-AZETIDINYL)-4-OXO-2-BUTENOIC ACID

RELATED APPLICATION

U.S. patent application Ser. No. 503,964, filed June 13, 1983, discloses antibacterial agents which comprise a β-lactam nucleus having a 3-acylamino substituent and in the 1-position a substituent of the formula

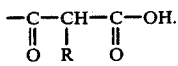

wherein R is hydrogen or alkyl.

BRIEF DESCRIPTION OF THE INVENTION

Compounds having the formula

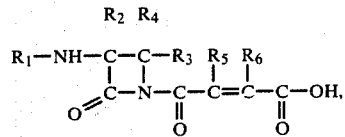

and salts and esters thereof, exhibit antibacterial activity. In formula I, and throughout the specification, the symbols are as defined below.

$R_1$ is an acyl group derived from a carboxylic acid;

$R_2$ is hydrogen or methoxy;

$R_3$ and $R_4$ are the same or different and each is hydrogen, alkyl, alkenyl, alkynyl, cycloalkyl, phenyl, substituted phenyl or a 4, 5, 6 or 7-membered heterocycle (referred to hereinafter as $R_x$) or one of $R_3$ and $R_4$ is hydrogen and the other is azido, halomethyl, dihalomethyl, trihalomethyl, alkoxycarbonyl, 2-phenylethenyl, 2-phenylethynyl, carboxyl, —CH$_2$X$_1$ [wherein $X_1$ is azido, amino (—NH$_2$), hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

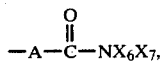

—S—X$_2$, or —O—X$_2$ (wherein A, X$_2$, X$_6$ and X$_7$ are as hereinafter defined)]. —S—X$_2$ or —O—X$_2$ [wherein X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

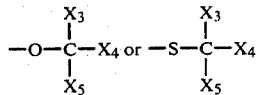

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

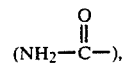

(substituted amino)carbonyl, or cyano (—C≡N)], or

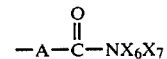

(wherein A is —CH=CH—, —(CH$_2$)$_n$—, —CH$_2$—O—, —CH$_2$—NH—, or —CH$_2$—S—CH$_2$, n is 0, 1 or 2, and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle); and $R_5$ and $R_6$ are the same or different and each is hydrogen or alkyl.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido, amino (—NH$_2$), halogen, hydroxy, carboxy, cyano, alkoxycarbonyl, aminocarbonyl, alkanoyloxy, alkoxy, phenyloxy, (substituted phenyl)oxy, $R_x$-oxy, mercapto, alkylthio, phenylthio, (substituted phenyl)thio, alkylsulfinyl, or alkylsulfonyl groups.

The terms "alkanoyl", "alkenyl", and 37 alkynyl" refer to both straight and branched chain groups. Those groups having 2 to 10 carbon atoms are preferred.

The terms "halogen" and "halo" refer to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, and p-nitrobenzyl esters.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), or carboxyl groups.

The expression "a 4,5,6 or 7-membered heterocycle" (referred to as "$R_x$") refers to substituted and unsubstituted, aromatic and non-aromatic groups containing one or more nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

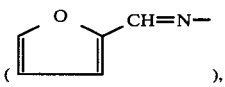

benzylideneamino and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihyrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)-amino]ethyl]-2-oxo-1-imidazolidinyl, 2-oxo-1-pyrrolidinyl, 2-oxo-3-osazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

Ther term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy, or amino ($-NH_2$).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

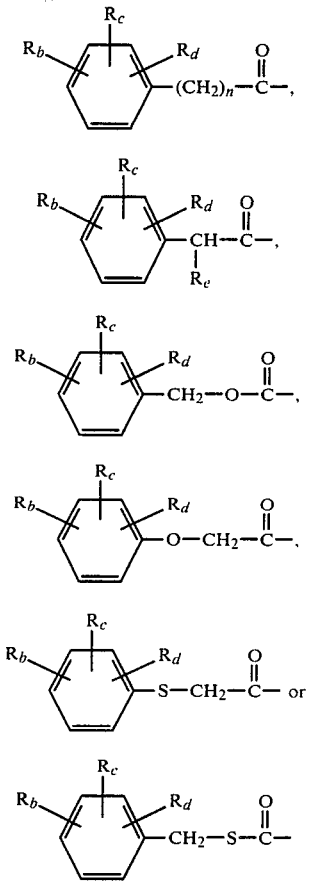

wherein n is 0, 1, 2, or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

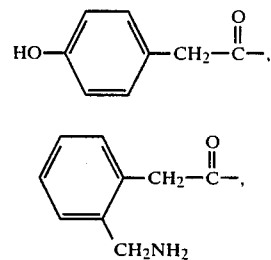

-continued

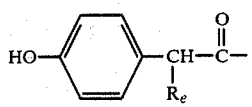

($R_e$ is preferably a carboxyl salt or sulfo salt) and

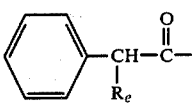

($R_e$ is preferably a carboxyl salt or sulfo salt).

(c) Heteroaromatic groups having the formula

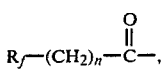

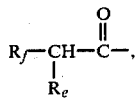

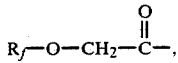

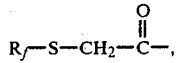

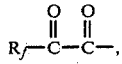

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

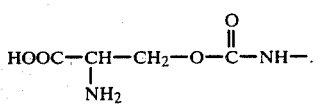

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

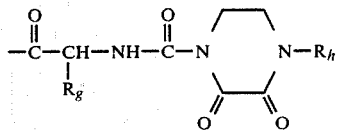

wherein $R_g$ is an aromatic group (including carbocyclic aromatics such as those of the formula

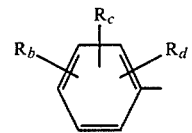

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

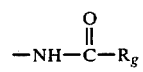

wherein $R_g$ is as defined above) or alkylcarbonylamino.

Preferred [[(4-substituted-2,3-dioxo-1-piperazinyl)-carbonyl]amino]arylacetyl groups include those wherein $R_h$ is ethyl, phenylmethyleneamino or 2-furylmethyleneamino.

(e) (Substituted oxyimino)arylacetyl groups having the formula

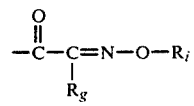

wherein $R_g$ is as defined above and $R_i$ is hydrogen, alkyl, cycloalkyl, alkylaminocarbonyl, arylaminocarbonyl (i.e.

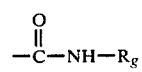

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

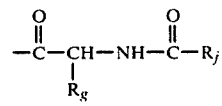

wherein $R_g$ is as defined above and $R_j$ is

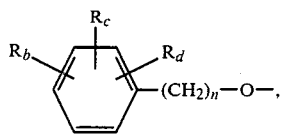

amino, alkylamino, (cyanoalkyl)amino, amido, alkylamido, (cyanoalkyl)amido,

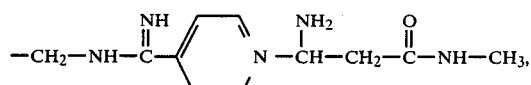

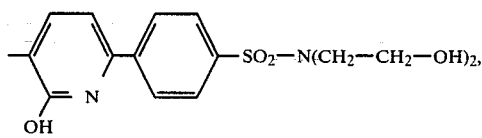

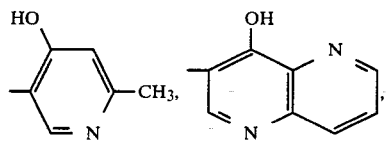

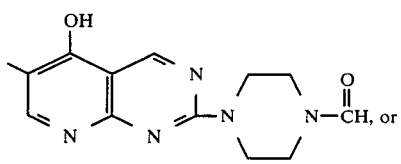

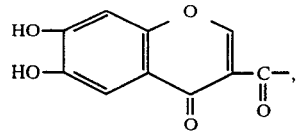

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

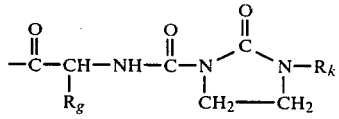

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The terms "salt" and "salts" refer to basic salts formed with inorganic and organic bases. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

As set forth throughout the specification, β-lactams having in the 1-position an ester of the group

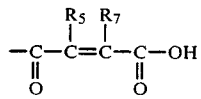

are contemplated as an integral part of this invention. Exemplary esters include alkyl, alkenyl, alkynyl, cycloalkyl, (cycloalkyl)alkyl, $R_x$-alkyl, trialkylsilylalkyl, mono-, di- or trihaloalkyl, hydroxyalkyl, alkoxyalkyl, carboxyalkyl, alkoxycarbonylalkyl, diphenylmethoxycarbonylalkyl, carbamoylalkyl, alkylcarbamoylalkyl, dialkylcarbamoylalkyl, indanyl, phenyl, substituted phenyl, phenylalkyl, (substituted phenyl)alkyl. $R_x$-carbonylalkyl,

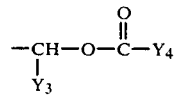

[wherein $Y_3$ is hydrogen, alkyl or phenyl and $Y_4$ is hydrogen, alkyl, cycloalkyl, (cycloalkyl)oxy, phenyl, or alkoxy, or together $Y_3$ and $Y_4$ are —(CH$_2$)$_2$—, —(CH$_2$)$_3$—,

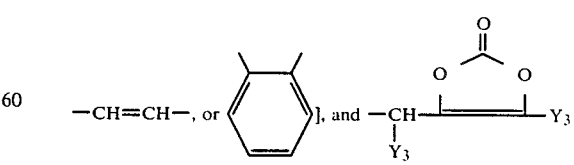

Hydrolyzable esters are those esters that can be hydrolyzed in vivo to give the parent carboxylic acid product; they exhibit the antibiotic acitivity of the parent carboxylic acid. Non-hydrolyzable esters (esters that do not hydrolze in vivo to the parent carboxylic acid) are contemplated for use in this invention as intermediates; some of them will also be active as antibiotics.

The 1-activating group of the β-lactams of this invention contains ethylenic unsaturation. The stereochemistry of the double bonded carbon atoms may be in either the cis or trans configuration.

β-Lactams having a

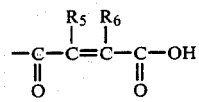

substituent (or an ester or salt thereof) in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins, (e.g., cephamycin C).

Also included within the scope of this invention are racemic mixtures which contain the above-described β-lactams.

Detailed Description of the Invention

The β-lactams of formula I, and salts thereof, have activity against a range of gram-negative and gram-positive organisms. The compounds of this invention can be used as agents to combat bacterial infections (including urinary tract infections and respiratory infections) in mammalian species, such as domesticated animals (e.g., dogs, cats, cows, horses, and the like) and humans.

The products of formula I can be prepared from a 3-protected amino-2-azetidinone having the formula

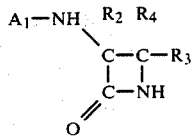

wherein the symbol "$A_1$" represents an amino protecting group (e.g., t-butoxycarbonyl, benzyloxycarbonyl, o-nitrophenylsulfenyl, etc.).

Those products of formula I wherein the stereochemistry of the double bonded carbon atoms is in the trans configuration are prepared by first silylating an azetidinone of formula II using, for example, monosilyltrifluoroacetamide (referred to hereinafter as MSTFA), trimethylsilylchloride/triethylamine, bis-trimethylsilyltrifluoroacetamide, or N-methyl-N-trimethylsilyltrifluoroacetamide. The resulting 1-silylated derivative can be reacted with a fumaric acid derivative having the formula

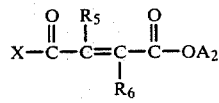

to yield a corresponding compound having the formula

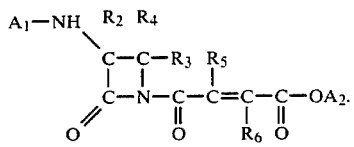

The symbol "X" represents a leaving group such as a halogen, and the symbol "$A_2$" represents a carboxyl protecting group.

The protecting groups $A_1$ and $A_2$ should be chosen so that it is possible to remove the $A_1$ group while leaving the $A_2$ group in place, and yielding a compound having the formula

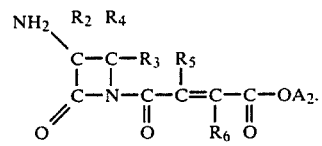

The deprotection techniques used are conventional, and will depend on the particular protecting group ($A_1$) present. Treatment with acid (e.g., formic acid or trifluoroacetic acid) cleaves a triphenylmethyl or a t-butoxycarbonyl protecting group. A benzyloxycarbonylamino protecting group can be cleaved by treatment with trimethylsilyl iodide. Treatment with phosgene or phosphorous pentachloride cleaves an amide protecting group. The compounds of formula V are novel intermediates, and as such, constitute an integral part of this invention.

Conventional acylation techniques can be used to prepare the products of formula I from a compound of formula V. Exemplary acylation techniques include reaction with a carboxylic acid ($R_1$—OH), or corresponding carboxylic acid halide or carboxylic acid anhydride. The reaction with a carboxylic acid proceeds most readily in the presence of a carbodiimide and a substance capable of forming an active ester in situ such as N-hydroxybenzotriazole. In those instances wherein the acyl group ($R_1$) contains reactive functionality (such as amino or carboxyl groups) it may be necessary to first protect those functional groups, then carry out the acylation reaction, and finally deprotect the resulting product. The resulting compound has the formula

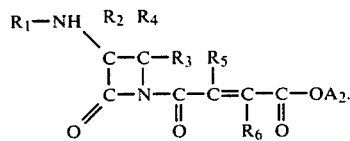

Deprotection of the carboxylic acid group of a compound of formula VI, followed by esterification (if desired), yields the desired product of formula I. It is also possible to prepare those products of this invention which are esters of a compound of formula I by utilizing the desired ester group as the protecting group $A_2$.

Those products of formula I wherein the stereochemistry of the double bonded atoms is in the cis configuration are prepared by first activating the ring nitrogen of an azetidinone of formula II with sec-butyl lithium and reacting the activated azetidinone with a maleic anhydride derivative having the formula

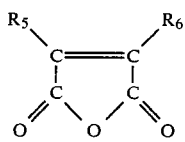   VII to obtain the corresponding compound having the formula

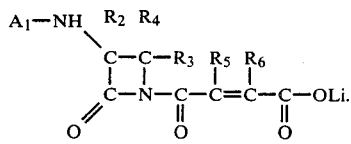   VIII

If $R_5$ and $R_6$ are both substituents other than hydrogen, the product of formula VIII is obtained as a mixture of compounds, in one of which the stereochemistry of the double bonded atoms is in the cis configuration, and in the other in the trans configuration. Conventional techniques can be used to separate the compounds.

Deprotection of a compound of formula VIII using art-recognized techniques as described above yields the corresponding compound having the formula

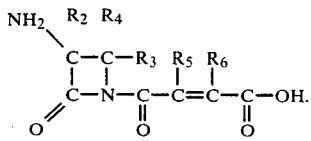   IX

Acylation of a compound of formula IX using conventional acylation techniques as described above yields the corresponding product of formula I wherein the stereochemistry of the double bonded carbon atoms is in the cis configuration.

Alternatively, products of formula I wherein $R_5$ is hydrogen can be prepared by first subjecting a compound of formula IV, wherein $R_5$ and $R_6$ are hydrogen, to ozonolysis to yield the corresponding compound having the formula

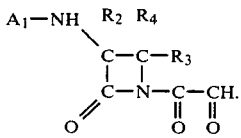   X

Reaction of a compound of formula X with a phosphorous compound having the formula

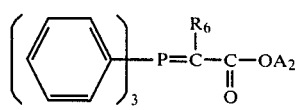   XI yields a separable mixture of the cis and trans isomers of the compound having the formula

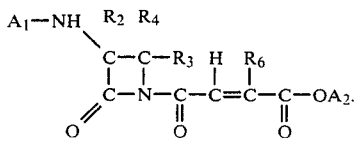   XII

After the isomers are separated by chromatography, they can be deprotected and acylated as described above to yield the desired products of formula I.

Methodology for the preparation of the starting 2-azetidinones of formula II is described in United Kingdom patent application 2,071,650, published Sept. 23, 1981. These azetidinones are obtainable using any one of numerous procedures.

Reacting an olefin having the formula

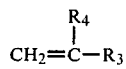   XIII with a halosulfonylisocyanate (preferably chlorosulfonylisocyanate) having the formula

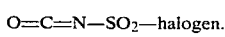   XIV yields an azetidinone having the formula

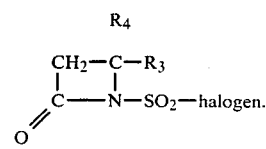   XV

Reductive hydrolysis of an azetidinone of formula XV yields an N-unsubstituted $\beta$-lactam having the formula

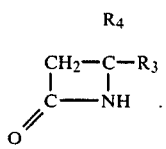   XVI

For a more detailed description of the above-described reaction sequence, reference can be made to the literature; see, for example, *Chem. Soc. Rev.*, 181 (1976) and *J. Org. Chem.* 35, 2043 (1970).

An azido group can be introduced in the 3-position of an azetidinone of formula XVI by reaction of the compound with an arylsulfonyl azide (such as toluenesulfonyl azide) to obtain an azetidinone having the formula

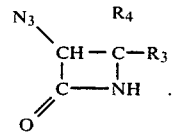   XVII

The reaction proceeds best by first protecting the azetidinone nitrogen with a silyl residue (e.g., t-butyldimethylsilyl, or t-butyldiphenylsilyl), then generating the anion at the 3-position of the nucleus with a strong organic base (e.g., lithium diisopropylamine) at a low temperature, and then treating the anion with toluenesulfonyl azide. The resulting intermediate is quenched with trimethylsilyl chloride, and subsequent acid hydrolysis or fluoride solvolysis of the N-protecting group yields the compound of formula XVII.

A 3-azido-2-azetidinone of formula XVII wherein $R_4$ is hydrogen can also be prepared by first reacting a primary amine having the formula

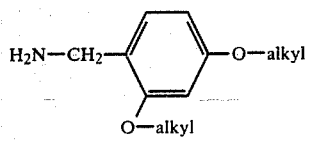

XVIII or

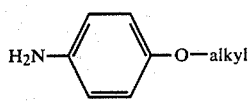

XIX with an aldehyde having the formula

XX (or a hemiacetal) to yield the corresponding Schiff base. A [2+2] cycloaddition reaction of the Schiff base with an activated form of α-azidoacetic acid yields a 3-azido-2-azetidinone having the formula

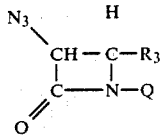

XXI wherein Q is

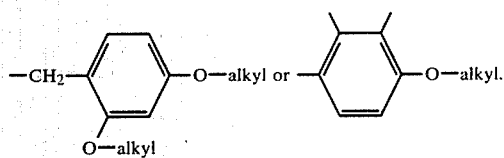

Oxidative removal of the 1-substituent yields the corresponding compound having the formula

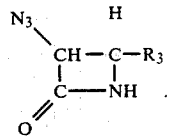

XXII

A 3-azido-2-azetidinone of formula XVII or XXII can be reduced to the corresponding 3-amino-2-azetidinone having the formula

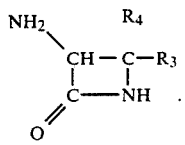

XXIII

The reduction can be accomplished by catalytic (e.g., palladium on charcoal, or platinum oxide) hydrogenation or with reducing agents such as zinc or triphenylphosphine. A 3-amino-2-azetidinone can be converted to a corresponding 3-protected amino-2-azetidinone of formula II using art-recognized techniques.

A compound of formula II wherein $R_3$ is hydrogen can also be obtained using a procedure analogous to that described above for the preparation of a 3-azido-2-azetidinone wherein $R_3$ is hydrogen. In place of an activated form of α-azidoacetic acid, an activated form of α-phthalimidoacetic acid is used, yielding a compound having the formula

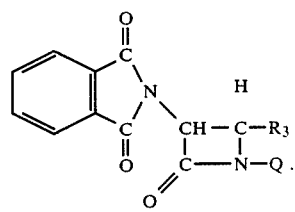

XXIV

Treatment of a compound of formula XXIV with base yields the corresponding 4α compound having the formula

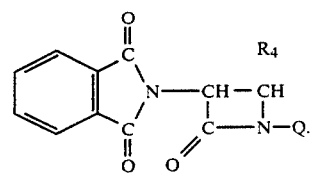

XXV

Reaction of a compound of formula XXIV or XXV with a reagent such as methyl hydrazine (to cleave the phthaloyl group), followed by the introduction of a protecting group on the 3-nitrogen substituent, and oxidative removal of the 1-protecting group will yield a compound of formula II wherein $R_2$ and $R_4$ are hydrogen.

The starting 2-azetidinones of formula II wherein $R_2$ is methoxy can be prepared by methoxylating the corresponding non-methoxylated compound of formula II. Chlorination of a nonmethoxylated compound of formula II yields a compound having the formula

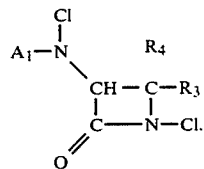

XXVI and can be accomplished by reaction of a compound of formula II with a reagent such as t-butyl hypochlorite, sodium hypochlorite, chlorine or other reagent useful for N-chlorinating amides. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of a compound of formula XXV with a methoxylating agent, e.g., an alkali metal methoxide, and subsequently adding a reducing agent such as trimethylphosphite, yields a compound having the formula

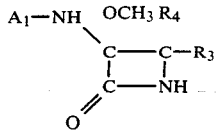

XXVII in combination with its enantiomers.

Additional methodology for the preparation of the starting 2-azetidinones of formula II is described in United Kingdom patent application No. 2,071,650, published Sept. 23, 1981. The cyclization of amino acids to yield 2-azetidinones is described as is the degradation of 6-aminopenicillanic acids and 7-aminopenicillanic acids to yield 2-azetidinones.

The following examples are specific embodiments of this invention.

EXAMPLE 1

(E)-4-Oxo-4-[(S)-2-oxo-3-[[(phenylmethoxy)carbonyl]-amino]-1-azetidinyl]-2-butenoic acid, ethyl ester (S)-3-[[(Phenylmethoxy)carbonyl]amino]-2-azetidinone (4.40 g) and 5 g of MSTFA were stirred for 1 hour in 30 ml of acetonitrile at 50° under an argon atmosphere. The resulting clear solution was evaporated and the oily residue dissolved in 20 ml of dichloromethane (absolute). After cooling to 0° C., 3.25 g of (E)-4-chloro-4-oxo-2-butenoic acid, ethyl ester in 20 ml of dichloromethane was added dropwise. Stirring for 3 hours and evaporating the solvent yielded the title compound as an oily residue. Purification on silica gel (dichloromethane/ethyl acetate (9:1) eluent) yielded the title compound as a white crystalline material, melting point 68° C.

IR(film): 1795 cm$^{-1}$ $^1$H-NMR (DMSO d$_6$, 90 MHz) $\delta = 1.27$ (t, 3H); 3.60 (dd, 1H); 3.97 (t, 1H); 4.24 (q, 2H); 4.91 (m, 1H broad); 5.1 (s, 2H); 7.21 (q, 2H); 7.4 (s, 5H); 8.19 (d, 1H broad) ppm.

EXAMPLE 2

[1(E); 3S]-4-[3-[[(1,1-Dimethylethoxy)carbonyl]-amino]-2-oxo-1-azetidinyl]-4-oxo-2-butenoic acid, ethyl ester Following the procedure of Example 1, but substituting 1.85 g of (S)-3-[[(t-butoxy)carbonyl]-amino]-2-azetidinone for (S)-3-[[(phenylmethoxy)-carbonyl]amino]-2-azetidinone, and utilizing 3.0 g of MSTFA, and 1.63 g of (E)-4-chloro-4-oxo-2-butenoic acid, ethyl ester, yielded the title compound as an oil.

IR(film) 1795 cm$^{-1}$ $^1$H-NMR (DMSO d$_6$, 90 Hz) $\delta = 1.42$ (s, 9H); 1.25 (t, 3H); 3.58 (dd, 1H); 3.96 (t, 1H); 4.20 (q, 2H); 7.24 (q, 2H); 8.26 (d, 1H broad) ppm.

EXAMPLE 3

(E)-4-[(3S-trans)-3-[[(2,2-Dimethylethoxy)carbonyl]-amino]-4-methyl-2-oxo-1-azetidinyl]-4-oxo-2-butenoic acid, ethyl ester Following the procedure of Example 1, but substituting (3S-trans)-3-[[(t-butoxy)carbonyl]-amino]-4-methyl-2-azetidinone for (S)-3-[[(phenylmethoxy)carbonyl]amino-2-azetidinone, yielded the title compound as an oil.

IR(film): 1800 cm$^{-1}$ $^1$H-NMR (COCl$_3$, 90 MHz): $\delta = 1.32$ (t, 3H); 1.42 (s, 9H); 1.62 (d, 3H); 4.25 (m, 2H); 5.83 (d, 1H); 7.37 (q, 2H) ppm.

EXAMPLE 4

[1(E); 3S]-4-(3-Amino-2-oxo-1-azetidinyl)-4-oxo-2-butenoic acid, ethyl ester, trifluoroacetate salt

[1(E); 3S]-4-[3-[[(1,1-Dimethylethoxy)-carbonyl]-amino]-2-oxo-1-azetidinyl]-4-oxo-2-butenoic acid, ethyl ester (2 g) was dissolved in 15 ml of trifluoroacetic acid and stirred for 15 minutes at 0° C. After adding ether, the title compound crystallized quantitatively from the solution as white crystals, melting point 138° C. (dec.).

IR(KBr): 1800 cm$^{-1}$

EXAMPLE 5

(E)-4-[(3S-trans)-3-Amino-4-methyl-2-oxo-1-azetidinyl]-4-oxo-butenoic acid, ethyl ester, trifluoroacetate salt (1:1)

Following the procedure of Example 4, but substituting (E)-4-[(3S-trans)-3-[[(1,1-dimethylethoxy)carbonyl]-amino]-4-methyl-2-oxo-1-azetidinyl]-4-oxo-2-butenoic acid, ethyl ester for [1(E); 3S]-4-[3-[[(1,1-Dimethylethoxy)carbonyl]amino]-2-oxo -1-azetidinyl]-4-oxo-2-butenoic acid, ethyl ester, yielded the title compound, melting point 79° C. (dec.).

IR(KBr): 1795 cm$^{-1}$ $^1$H-NMR (DMF-d$_7$, 90 MHz) $\delta = 1.28$ (t, 3H); 1.64 (d, 3H); 4.28 (q, 2H); 4.45 (m, 1H); 4.7 (d, 1H); 5.64 (3H broad); 7.25 (q, 2H)

EXAMPLE 6

[3S-[3$\alpha$(Z),4$\beta$]]-4-[3-[[(2-Amino-4-thiazolyl)-(methoxyimino)acetyl]amino]-4-methyl-2-oxo-1-azetidinyl]]-4-oxo-2-butenoic acid, ethyl ester (Z)-2-Amino-$\alpha$-(methoxyimino)-4-thiazoleacetic acid, (324.9 mg) and 242.2 mg of N-hydroxybenzotriazole were dissolved in 5 ml of dimethylformamide (anhydrous) and while stirring at 0° C. a solution of 333 mg of dicyclohexylcarbodiimide in 3 ml of dimethylformamide was added dropwise and stirring was continued for 1 hour.

(E)-4-[(3S-trans)-3-Amino-4-methyl-2-oxo-1-azetidinyl]-4-oxo-butenoic acid, ethyl ester, trifluoroacetate salt (1:1) (550 mg) was dissolved in 10 ml of dimethylformamide at 0° C. and 2 g of MSTFA was added. After stirring for 30 minutes, the reaction solution was added to the reaction solution containing the acid and the mixture was stirred at 0° C. for 2 hours. Dicyclohexylurea was filtered off and the dimethylformamide solution was evaporated. The residue was dissolved in 30 ml of ethyl acetate, and 3 ml of isopropanol was added and the solution was stirred for 10 minutes. The solution was then filtered and extracted with 30 ml of 1N NaHCO₃/ice water. The organic phase was evaporated and the oily residue was chromatographed on silica eluting with ethyl acetate/ether (8:2). The title compound was obtained as a powder, melting point 89° C., (dec.).

IR(KBr): 1800 cm⁻¹

¹H-NMR (DMSO d₆, 90 MHz) δ=1.22 (t, 3H); 1.48 (d, 3H); 3.85 (s, 3H); 4.23 (q, 2H); 4.6 (1H, m); 6.8 (s, 1H); 7.25 (q, 2H); 7.27 (s broad, 2H); 9.32 (d, 1H)

EXAMPLE 7

(Z)-4-Oxo-4-[(S)-2-oxo-3-[[(phenylmethoxy)carbonyl]amino]-1-azetidinyl]-2-butenoic acid, lithium salt In an argon atmosphere, 4.8 g of (S)-3-[[(phenylmethoxy)carbonyl]amino]-2-azetidinone in 20 ml of tetrahydrofuran (anhydrous) was added (at −70° C.) 18 ml of a 12% solution of sec-butyl lithium in cyclohexane. After 20 minutes of stirring, a solution of 2.5 g of maleic anhydride in 50 ml of tetrahydrofuran was added dropwise. Stirring was continued for 1 hour at −70° C. and the reaction solution was allowed to attain room temperature. Tetrahydrofuran was distilled off and the white solid residue was stirred with 200 ml of ether and isolated after filtration, yielding 7.2 g of the title compound as a white powder.

IR(KBr): 1800 cm⁻¹

¹H-NMR (DMSO d₆, 90 MHz): δ=3.54–4 (m, 2H broad); 4.90 (m, 1H); 5.08 (s, 2H); 6.32 (q, 2H); 7.4 (s, 5H); 8.28 (d, 1H broad)

EXAMPLE 8

(Z)-4-[(3S-trans)-3-[[(1,1-Dimethylethoxy)-carbonyl]amino]-4-methyl-2-oxo-1-azetidinyl]-4-oxo-2-butenoic acid, lithium salt In an argon atmosphere, 0.9 g of (3S-trans)-3-[[(t-butoxy)carbonyl]amino]-4-methyl-2-azetidinone dissolved in 100 ml of ether was cooled to −70° C. and 3.5 ml of a 12% solution of sec-butyl lithium in cyclohexane was added dropwise under stirring. After 30 minutes of stirring, a solution of 0.5 g maleic anhydride dissolved in 20 ml of ether was added slowly. After 1 hour at −70° C. the reaction was allowed to attain room temperature. During that time, a white precipitate was formed. The title compound (1.2 g) was isolated after filtration as a white powder.

IR(KBr): 1798 cm⁻¹

¹H-NMR (DMSO d₆, 90 MHz) β=1.32 (s, 9H); 1.46 (d, 3H); 4.1 (m, 2H); 6.35 (q, 2H); 7.8 (d, 1H broad)

EXAMPLE 9

(Z)-4-[(3S-trans)-3-[[(1,1-Dimethylethoxy)carbonyl]amino]-4-methyl-2-oxo-1-azetidinyl]-2-methyl-4-oxo-2-butenoic acid, lithium salt, and (Z)-4-[(3S-trans)-3-[[(1,1-Dimethylethoxy)carbonyl]amino]-4-methyl-2-oxo-1-azetidinyl]-3-methyl-4-oxo-2-butenoic acid, lithium salt Following the procedure of Example 8, but substituting methylmaleic anhydride for maleic anhydride, yielded a mixture of the title compounds.

EXAMPLE 10

(Z)-4-[(3S-trans)-3-[[(1,1-Dimethylethoxy)carbonyl]amino]-4-methyl-2-oxo-1-azetidinyl]-2,3-dimethyl-4-oxo-2-butenoic acid, lithium salt and (E)-4-[(3S-trans)-3-[[(1,1-Dimethylethoxy)carbonyl]amino]-4-methyl-2-oxo-1-azetidinyl]-2,3-dimethyl-4-oxo-2-butenoic acid, lithium salt Following the procedure of Example 8, but substituting dimethylmaleic anhydride for maleic anhydride, yielded a mixture of the title compounds.

What is claimed is:

1. A compound having the formula $$R_1-NH-\underset{\underset{O}{\overset{\|}{C}}}{\overset{R_2}{\underset{|}{C}}}-\underset{|}{\overset{R_4}{\underset{|}{C}}}-R_3 \quad \underset{\underset{O}{\overset{\|}{C}}-N-\underset{|}{\overset{R_5}{C}}-\underset{|}{\overset{R_6}{C}}=\underset{|}{C}-\underset{\overset{\|}{O}}{C}-OH,$$

or a pharmaceutically acceptable ester or basic salt thereof, wherein $R_1$ is an acyl group derived from a carboxylic acid;
$R_2$ is hydrogen or methoxy;
$R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, —CH₂X₁, carboxyl, —S—X₂, —O—X₂, $$-A-\overset{O}{\overset{\|}{C}}-NX_6X_7, \quad -O-\underset{\underset{X_5}{|}}{\overset{X_3}{\overset{|}{C}}}-X_4 \text{ or } -S-\underset{\underset{X_5}{|}}{\overset{X_3}{\overset{|}{C}}}-X_4;$$

wherein $X_1$ is azido, amino, hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano, $$-A-\overset{O}{\overset{\|}{C}}-NX_6X_7,$$

—S—X₂ or —O—X₂; X₂ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH=CH—, —(CH₂)ₙ—, —CH₂—O—, —CH₂—NH— or —CH₂—S—CH₂—; n is 0, 1 or 2; and X₆ and X₇ are the same of different and each is hydrogen, alkyl, phenyl or substituted phenyl, or X₆ is hydrogen and X₇ is amino, substituted amino, acylamino or alkoxy, or $X_6$ and $X_7$ when taken together with the nitrogen atom to which they are attached form a 4, 5, 6, or 7-membered heterocycle; and $R_5$ and $R_6$ are the same or different and each is hydrogen or alkyl;

wherein the terms "alkyl" and "alkoxy" refer to groups having 1 to 10 carbon atoms;

the term "cycloalkyl" refers to groups having 3, 4, 5, 6 or 7 carbon atoms:

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

the terms "alkanoyl", alkenyl" and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, or carboxyl groups;

the term "heteroaryl" refers to pyridinyl, furanyl, pyrrolyl, thienyl, 1,2,3-triazolyl, 1,2,4-triazolyl, imidazolyl, thiazolyl, pyrimidinyl, oxazolyl, triazinyl, or tetrazolyl, or one of the above groups substituted with one or more halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino, benzylideneamino or substituted alkyl, wherein the alkyl group has 1 to 4 carbons, groups;

the term "a 4,5,6 or 7-membered heterocycle" refers to pyridinyl, furanyl, pyrrolyl, thienyl 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or to one of the above groups substituted with one or more oxo, halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino, benzylideneamino or substituted alkyl, wherein the alkyl group has 1 to 4 carbons, groups;

the term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy, or amino.

2. A compound in accordance with claim 1 wherein $R_2$ is hydrogen.

3. A compound in accordance with claim 2 wherein $R_3$ and $R_4$ are each independently hydrogen or alkyl.

4. A compound in accordance with claim 2 wherein $R_3$ and $R_4$ are each independently hydrogen or methyl.

5. A compound in accordance with claim 2 wherein $R_5$ and $R_6$ are each hydrogen.

6. A compound in accordance with claim 2 wherein $R_1$ is

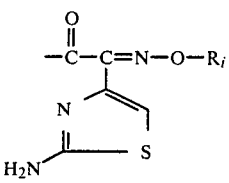

and $R_i$ is methyl, ethyl, carboxymethyl, 1-carboxy-1-methylethyl, 2,2,2-trifluoroethyl or 1-carboxycyclopropyl.

7. A compound in accordance with claim 2 wherein $R_1$ is

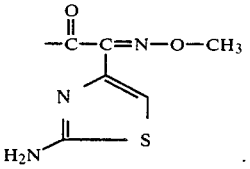

8. A compound in accordance with claim 2 wherein $R_1$ is

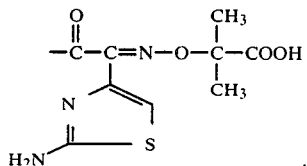

* * * * *

UNITED STATES PATENT AND TRADEMARK OFFICE
CERTIFICATE OF CORRECTION

PATENT NO. : 4,551,277          Page 1 of 5

DATED : November 5, 1985

INVENTOR(S) : Uwe D. Treuner

It is certified that error appears in the above-identified patent and that said Letters Patent is hereby corrected as shown below:

Column 1, before the second structural formula, please add "I".

Column 1, the structural formula between lines 20 and 25, the groups "$R_2$" and "$R_4$" are connected to the carbon atom immediately beneath them by the bond "$\equiv$".

Column 9, structural formula II, the groups "$R_2$" and "$R_4$" are connected to the carbon atom immediately beneath them by the bond "$\equiv$".

Column 10, structural formula IV, the groups "$R_2$" and "$R_4$" are connected to the carbon atom immediately beneath them by the bond "$\equiv$".

Column 10, structural formula V, the groups "$R_2$" and "$R_4$" are connected to the carbon atom immediately beneath them by the bond "$\equiv$".

Column 10, structural formula VI, the groups "$R_2$" and "$R_4$" are connected to the carbon atom immediately beneath them by the bond "$\equiv$".

UNITED STATES PATENT AND TRADEMARK OFFICE
CERTIFICATE OF CORRECTION

PATENT NO. : 4,551,277  Page 2 of 5

DATED : November 5, 1985

INVENTOR(S) : Uwe D. Treuner

It is certified that error appears in the above-identified patent and that said Letters Patent is hereby corrected as shown below:

Column 11, structural formula VIII, the groups "$R_2$" and "$R_4$" are connected to the carbon atom immediately beneath them by the bond "$\equiv$".

Column 11, structural formula IX, the groups "$R_2$" and "$R_4$" are connected to the carbon atom immediately beneath them by the bond "$\equiv$".

Column 11, structural formula X, the groups "$R_2$" and "$R_4$" are connected to the carbon atom immediately beneath them by the bond "$\equiv$".

Column 12, structural formula XII, the groups "$R_2$" and "$R_4$" are connected to the carbon atom immediately beneath them by the bond "$\equiv$".

Column 12, structural formula XV, the group "$R_4$" is connected to the carbon atom immediately beneath it by the bond "$\equiv$".

UNITED STATES PATENT AND TRADEMARK OFFICE
CERTIFICATE OF CORRECTION

PATENT NO. : 4,551,277

DATED : November 5, 1985

INVENTOR(S) : Uwe D. Treuner

It is certified that error appears in the above-identified patent and that said Letters Patent is hereby corrected as shown below:

Column 12, structural formula XVI, the group "$R_4$" is connected to the carbon atom immediately beneath it by the bond "$\equiv$".

Column 12, structural formula XVII, the group "$R_4$" is connected to the carbon atom immediately beneath it by the bond "$\equiv$".

Column 13, structural formula XXI, the group "H" is connected to the carbon atom immediately beneath it by the bond "$\equiv$".

Column 13, structural formula XXII, the group "H" is connected to the carbon atom immediately beneath it by the bond "$\equiv$".

Column 14, structural formula XXIII, the group "$R_4$" is connected to the carbon atom immediately beneath it by the bond "$\equiv$".

UNITED STATES PATENT AND TRADEMARK OFFICE
CERTIFICATE OF CORRECTION

PATENT NO. : 4,551,277

DATED : November 5, 1985

INVENTOR(S) : Uwe D. Treuner

It is certified that error appears in the above-identified patent and that said Letters Patent is hereby corrected as shown below:

Column 14, structural formula XXIV, the group "H" is connected to the carbon atom immmediately beneath it by the bond "≡".

Column 14, structural formula XXV, the group "$R_4$" is connected to the carbon atom immediately beneath it by the bond "≡".

Column 14, structural formula XXVI, the group "$R_4$" is connected to the carbon atom immmediately beneath it by the bond "≡".

Column 15, structural formula XXVII, the groups "$OCH_3$" and "$R_4$" are connected to the carbon atom immediately beneath them by the bond "≡".

Column 18, the structural formula of claim 1, the groups "$R_2$" and "$R_4$" are connected to the carbon atom immediately beneath them by the bond "≡".

Column 2, line 43, delete "37" and add quotation marks in its place.

UNITED STATES PATENT AND TRADEMARK OFFICE
CERTIFICATE OF CORRECTION

PATENT NO. : 4,551,277  Page 5 of 5

DATED : November 5, 1985

INVENTOR(S) : Uwe D. Treuner

It is certified that error appears in the above-identified patent and that said Letters Patent is hereby corrected as shown below:

Column 3, line 32, correct the spelling of the word "ox̲azolidinyl".

Column 3, line 38, "Ther" should be --The--.

Column 7, line 55, "$-N\}CH-R_g$" should be -- $-N=CH-R_g$ --.

Column 16, in the title of Example 3, "2,2-Dimethylethoxy" should be -- 1,1-Dimethylethoxy --.

Column 17, line 54, "$\beta$" should be -- $\delta$ --.

Signed and Sealed this

Twenty-second Day of April 1986

[SEAL]

Attest:

DONALD J. QUIGG

Attesting Officer          Commissioner of Patents and Trademarks